United States Patent
Baudino

(10) Patent No.: US 6,950,709 B2
(45) Date of Patent: Sep. 27, 2005

(54) LOW IMPEDANCE IMPLANTABLE EXTENSION FOR A NEUROLOGICAL ELECTRICAL STIMULATOR

(75) Inventor: Michael D. Baudino, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/686,108

(22) Filed: Oct. 15, 2003

(65) Prior Publication Data

US 2004/0078070 A1 Apr. 22, 2004

Related U.S. Application Data

(62) Division of application No. 09/893,851, filed on Jun. 28, 2001, now Pat. No. 6,671,544.

(51) Int. Cl.[7] ................................................. A61N 1/02
(52) U.S. Cl. ..................................................... 607/116
(58) Field of Search .......................... 607/2, 115–117, 607/122

(56) References Cited

U.S. PATENT DOCUMENTS

| | | | |
|---|---|---|---|
| 4,154,050 A | 5/1979 | Nation | 57/200 |
| 4,355,646 A | 10/1982 | Kallok et al. | 607/122 |
| 4,411,276 A | 10/1983 | Dickhudt et al. | 604/116 |

(Continued)

FOREIGN PATENT DOCUMENTS

| | | | | |
|---|---|---|---|---|
| WO | WO 00/64535 A1 | 11/2000 | .......... | A61N/1/375 |
| WO | WO 01/00274 A1 | 1/2001 | ............ | A61N/1/08 |

OTHER PUBLICATIONS

"MatWeb: Material Property Data", Online Material Data Sheets, http://www.matweb.com, 2005□□Platinum, Titanium, Aluminum, Copper, 8 pages.*

MatWeb Material Property Data, data sheets for MP35N, Gold, and Silver, from www.matweb.com, Sep. 5, 2004, Pp. 1–6.*

Brochure, "Implatable Neurostimulation Systems : Effective, Reliable and Flexible Solutions for Simple and Complex Pain," Medtronics, Inc., (1998).

Brochure, "Medtronic 7495 Extension Kit for Stimulation of the Brain, Spinal Cord, or Peripheral Nerves Implant Manual", Medtronic, Inc., 41 pp. (Sep. 25, 2000).

Brochure, "Implantable Neurostimulation Systems: Effective, reliable and flexible solutions for simple and complex pain," *Medtronic, Inc.*, (1998).

Brochure, "Medtronic 7495 Extension Kit For Stimulation of the Brain,Spinal Cord, or Peripheral Nerves Implant Manual," *Medtronic, Inc.*, 41 pgs. (Sep. 25, 2000).

*Primary Examiner*—Carl Layno
(74) *Attorney, Agent, or Firm*—Stephen W. Bauer; John W. Albrecht; Thomas G. Berry

(57) ABSTRACT

A medical device known as an implantable neurostimulation system is configured for implanting in humans to deliver a therapeutic electrical stimulation to tissue to treat a variety of medical conditions such as pain, movement disorders, pelvic floor disorders, and many other conditions. The implantable neurostimulation has a housing, a power supply carried in the housing, stimulation electronics coupled to the battery and coupled to a neurostimulator connector block, a stimulation lead, and a lead extension. The lead extension is electrically coupleable between the neurostimulation connector block and the stimulation lead. The extension conductor is composed of an outer surface and an inner core. The outer surface has an outer impedance and the inner core has a core impedance that is substantially lower than the outer impedance. Many embodiments of the low impedance lead extension are possible.

4 Claims, 4 Drawing Sheets

U.S. PATENT DOCUMENTS

| | | | |
|---|---|---|---|
| 4,573,481 A | 3/1986 | Bullara | 607/118 |
| 4,640,983 A | 2/1987 | Comte | 174/119 R |
| 4,677,989 A | 7/1987 | Robblee | 607/116 |
| 4,860,446 A | 8/1989 | Lessar et al. | 29/858 |
| 4,947,866 A * | 8/1990 | Lessar et al. | 607/116 |
| 5,040,544 A | 8/1991 | Lessar et al. | 607/122 |
| 5,324,328 A | 6/1994 | Li et al. | 607/129 |
| 5,330,521 A | 7/1994 | Cohen | 607/122 |
| 5,417,719 A | 5/1995 | Hull et al. | 607/46 |
| 5,423,881 A | 6/1995 | Breyen et al. | 607/122 |
| 5,483,022 A | 1/1996 | Mar | 174/128.1 |
| 5,562,722 A | 10/1996 | Raez et al. | 607/117 |
| 5,760,341 A * | 6/1998 | Laske et al. | 174/126.2 |
| 5,931,862 A | 8/1999 | Carson | 607/120 |
| 6,061,598 A | 5/2000 | Verness et al. | 607/122 |
| 6,119,042 A | 9/2000 | Verness et al. | 607/122 |
| 6,192,279 B1 | 2/2001 | Barreras, Sr. et al. | 607/117 |
| 6,216,045 B1 | 4/2001 | Black et al. | 607/122 |
| 6,233,488 B1 | 5/2001 | Hess | 607/58 |
| 6,343,233 B1 | 1/2002 | Werner et al. | 607/119 |
| 6,430,442 B1 | 8/2002 | Peters et al. | 607/37 |
| 2003/0032997 A1 | 2/2003 | Pianca et al. | 607/117 |

\* cited by examiner

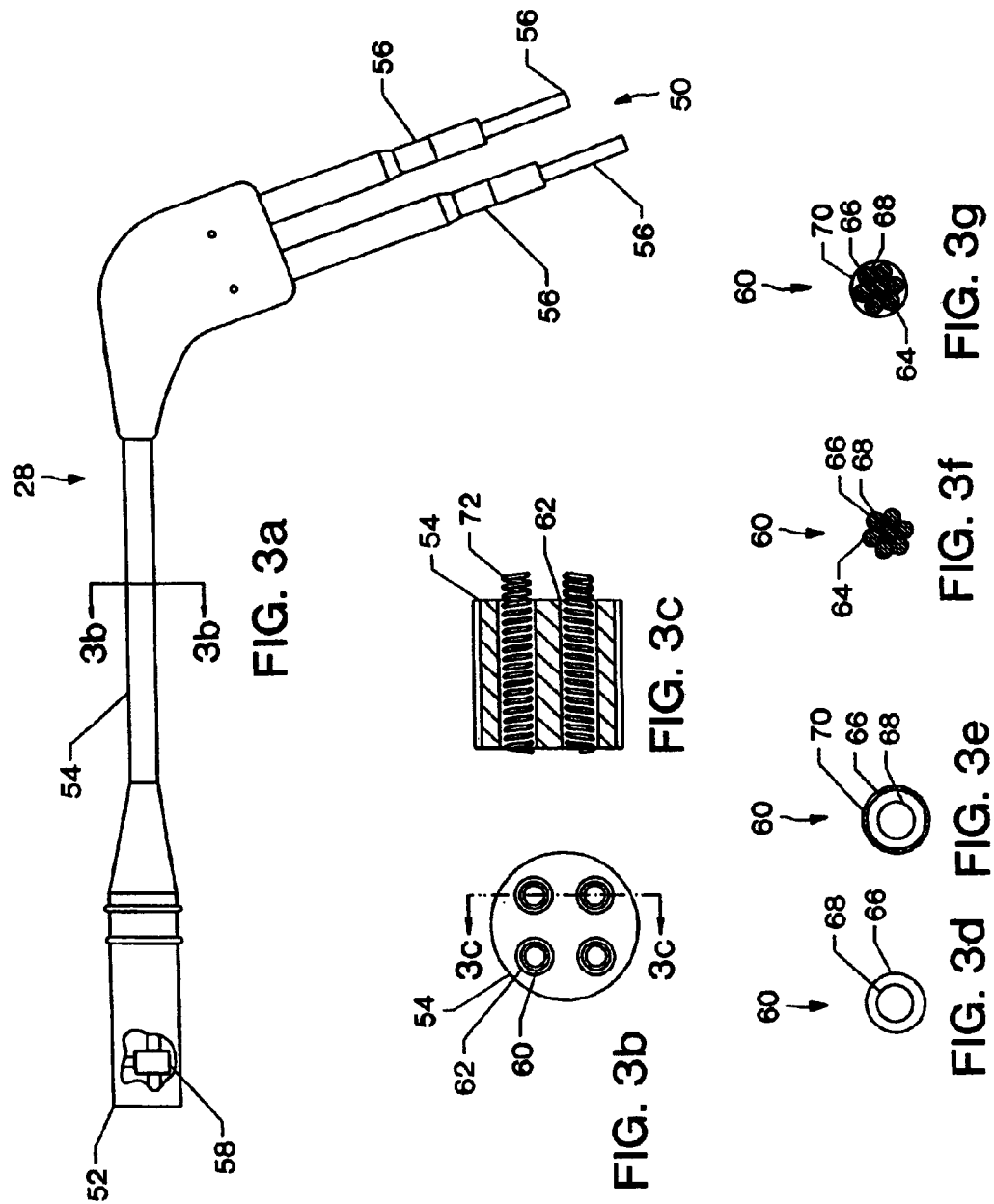

LOW IMPEDANCE IMPLANTABLE EXTENSION FOR A NEUROLOGICAL ELECTRICAL STIMULATOR

RELATED APPLICATION

This application is a divisional of prior application Ser. No. 09/893,851, filed Jun. 28,2001, now U.S. Pat. No. 6,671,544.

BACKGROUND OF THE INVENTION

This disclosure relates to a medical device and more particularly to implantable neurological electrical stimulators and implantable electrical stimulation leads.

The medical device industry produces a wide variety of electronic and mechanical devices for treating patient medical conditions such as pacemakers, defibrillators, neurostimulators, and therapeutic substance delivery pumps. Medical devices can be configured to be surgically implanted or connected externally to the patient receiving treatment. Clinicians use medical devices alone or in combination with therapeutic substance therapies and surgery to treat patient medical conditions. For some medical conditions, medical devices provide the best and sometimes the only therapy to restore an individual to a more healthful condition and a fuller life. One type of medical device is an implantable neurological stimulation system that can be used to treat conditions such as pain, movement disorders, pelvic floor disorders, gastroparesis, and a wide variety of other medical conditions. The neurostimulation system typically includes a neurostimulator, a stimulation lead, and an extension such as shown in Medtronic, Inc. brochure "Implantable Neurostimulation System" (1998).

Previous extensions are typically formed using a solid conductor formed from a material that is a reasonably good compromise between the mechanical properties required to form electrical connections and the conductive properties required to efficiently conduct the stimulation signal from the neurostimulator to the stimulation lead. The compromise of material used in a solid conductor results in higher impedance than is desired. The extension's higher impedance than desired can result in increased power consumption and decreased battery life. An example of an extension that uses a solid conductor is shown in Medtronic, Inc. brochure "Model 7495 Extension Kit for Stimulation of the Brain, Spinal Cord, or Peripheral Nerves" (2000). An example of a low impedance lead used for cardiac pacing and defibrillation typically having only one or two conductors is shown in U.S. Pat. No. 5,330,521 "Low Resistance Implantable Electrical Leads" by Cohen (Jul. 19, 1994).

For the foregoing reasons, there is a need for a low impedance extension that decreases power consumption and has many other improvements.

SUMMARY OF THE INVENTION

A low impedance extension for an implantable neurological electrical stimulator embodiment reduces energy consumption and has many other improvements. The low impedance extension has a conductor composed of an outer surface and an inner core. The outer surface has an outer impedance and the inner core has a core impedance that is substantially lower than the outer impedance. The low impedance extension has an extension proximal end, an extension distal end and an extension body. The extension proximal end has at least one proximal contact coupleable to an implantable neurostimulator connector block and an extension distal end having at least one extension distal contact coupleable to the lead proximal contact. The extension conductor is contained in the extension body to electrically connect the extension distal contact with the extension proximal contact. Many embodiments of the low impedance extension are possible.

BRIEF DESCRIPTION OF THE DRAWINGS

FIG. 3a shows a low impedance extension embodiment;

FIG. 3b shows a cross section of the low impedance extension body multi-lumen embodiment;

FIG. 3c shows a longitudinal cross section of an extension conductor multi-lumen embodiment;

FIG. 3d shows a cross-section of an extension conductor without insulator embodiment;

FIG. 3e shows a cross-section of an extension conductor with insulator embodiment;

FIG. 3f shows a cross-section of a stranded extension conductor embodiment;

FIG. 3g shows a cross-section of a stranded extension conductor with insulator embodiment;

DETAILED DESCRIPTION OF THE PREFERRED EMBODIMENTS

Figure 1:
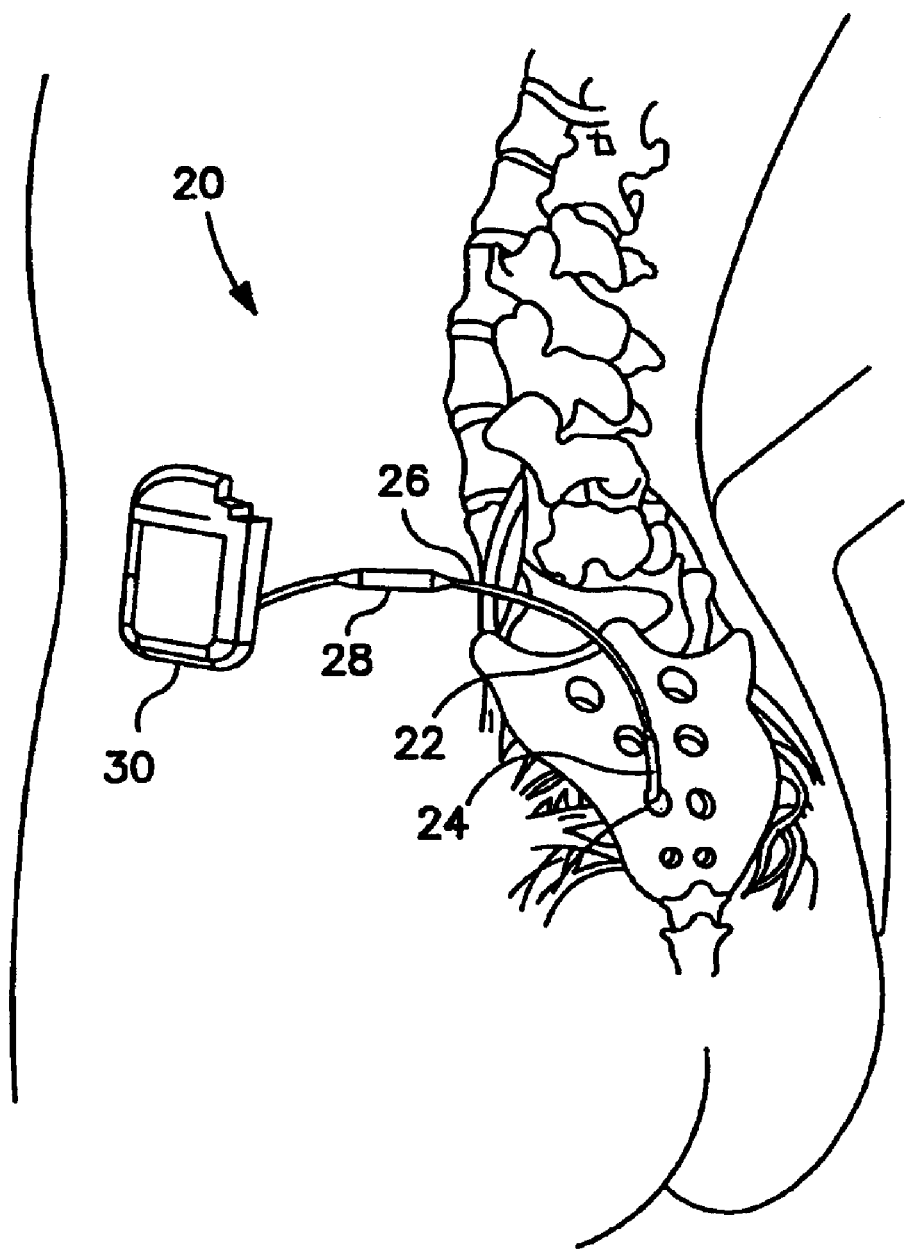
FIG. 1 shows the environment of an implantable therapeutic substance delivery device embodiment.

FIG. 1 shows the environment of an implantable medical device known as an implantable neurological electrical stimulation system 20. The neurological stimulation system 20 can be used for a wide variety of therapies such as pain, movement disorders, pelvic floor disorders, gastroparesis, and many other medical conditions. Implantation of the neurological stimulation system 20 typically begins with either percutaneous or surgical implantation of a stimulation lead 22 typically while the patient is under local anesthetic. Once the stimulation lead 22 has been implanted and positioned, the stimulation lead's distal end 24 is typically anchored into position to minimize movement of the stimulation lead 22 after implantation. The stimulation lead's proximal end 26 is connected to a lead extension 28 that has been tunneled to the location where a neurological electrical stimulator, also known as a neurostimulator 30 is to be implanted. The lead extension 28 is connected to the neurostimulator 30 and the neurostimulator 30 is typically implanted into a subcutaneous pocket at a site selected after considering clinician and patient preferences. The neurostimulator 30 can be programmed to generate a stimulation signal with a voltage amplitude typically in the range from about 0 V to about 10.5 V; a pulse width typically in the range from about 30 $\mu$S to about 450 $\mu$S; and a pulse rate typically in the range from about 2 Hz to about 180 Hz.

Figure 2:
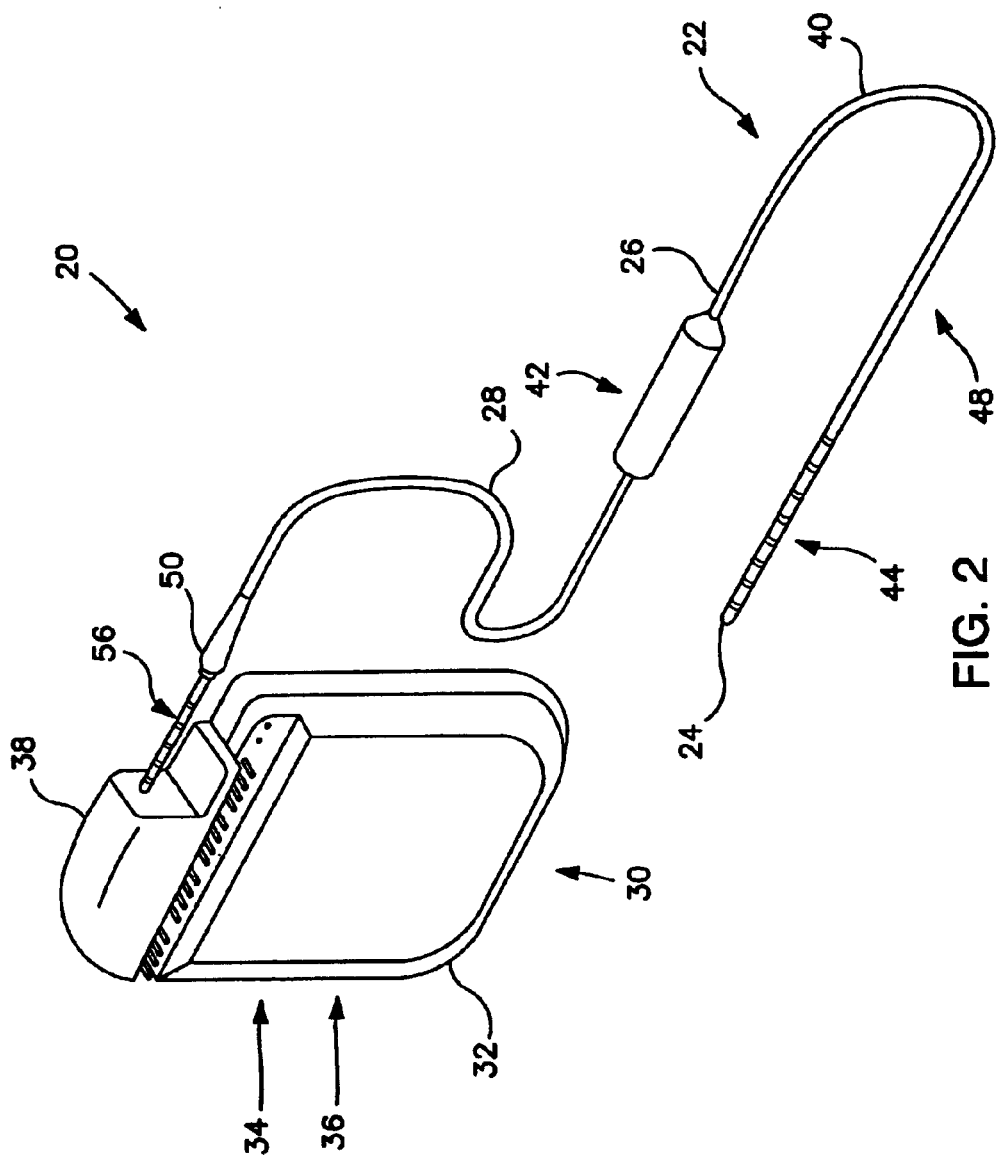
FIG. 2 shows a neurostimulation system embodiment.

FIG. 2 shows an implantable neurostimulation system 20 having a low impedance extension 28 comprising an implantable neurostimulator 30, a stimulation lead 22, and a lead extension 28. The implantable neurostimulator 30 has a housing 32, a power supply 34 such as a battery carried in the housing 32, and stimulation electronics 36 coupled to the power supply 34 and coupled to a connector block 38. The stimulation lead 22 has a lead proximal end 26, a lead distal end 24, and a lead body 40. The lead proximal end 26 has at least one electrical contact 42 and the lead distal end 24 has at least one stimulation electrode 44. There is at least one lead conductor 48 contained in the lead body 40 that electrically connects the lead electrical contact 42 to the stimulation electrode 44.

FIGS. 3a–3g show various low impedance extension 28 embodiments. The lead extension 28 has an extension proximal end 50, an extension distal end 52, and an extension body 54. The extension proximal end 50 has at least one proximal contact 56 coupleable to the implantable neurostimulator connector block 38. The extension distal end 52 has at least one extension distal contact 58 coupleable to the lead proximal electrical contact 42. There is at least one extension conductor 60 contained in at least one lumen 62 of the extension body 54 electrically connecting the extension distal contact 58 with the extension proximal contact 56. In some embodiments such as shown in FIGS. 3f and 3g, more than one wire strand 64 can be used to form a single extension conductor 60. Functionally, the lead extension 28 serves as a means for lead extension coupleable between the implantable neurostimulator connector block 38 and the lead proximal contact 42 to electrically connect the neurostimulator 30 to the stimulation lead 22.

The extension conductor 60 is composed of an outer surface 66 and an inner core 68. The outer surface 66 has an outer impedance and the inner core 68 has a core impedance that is substantially lower than the outer impedance. The resistivity ratio of the outer surface 66 to the inner core 68 is at least about 2:1. The low impedance conductor 60 resistance is in the range from about 0.05 to 0.3 ohms per centimeter of extension length. Resistance can be calculated using the formula $$R = \frac{\rho L}{A}$$

where R is resistance in ohms, ρ is resistivity in ohm-centimeters, L is conductor length in centimeters, and A is conductor cross-section area in centimeters squared. Functionally, the extension conductor 60 serves as a means for extension of electrical connectivity that has an outer surface 66 selected for mechanical properties and an inner core 68 selected for electrical conductivity with an impedance substantially less than the outer surface 66. The extension conductor 60 can be constructed of drawn filled tubing. The extension conductor 60 can have an outer insulator 70 surrounding the outer surface 66 of the extension conductor 60 (FIG. 3e). The outer insulator 70 can be composed of a wide variety of materials with electrically insulating properties such as fluoropolymer, polyurethane, silicone, polyimide and the like.

The outer surface 66 provides the mechanical properties of the extension conductor 60 such as corrosion resistance and fatigue life. The outer surface 66 can be composed of a wide variety of materials that provide the desired mechanical characteristics such as nickel, cobalt, chrome, molybdenum alloy, stainless steel, and the like. The outer surface 66 has a resistivity of greater than about 25 micro ohm-centimeter. Functionally, the outer surface 66 serves as a means for outer surface selected for the mechanical properties of flexibility and electrical connection formation.

The inner core 68 provides the low impedance properties of the extension conductor 60. The inner core 68 can be composed of a wide variety of materials having low impedance properties such as silver, silver alloy, gold, copper, platinum, iridium, tantalum, aluminum, and the like. The inner core 68 has a resistivity of less than about 12.5 micro ohm-centimeter. Functionally, the inner core 68 serves as a means for conductivity having a core impedance that is substantially lower than the outer impedance.

Figure 4A:
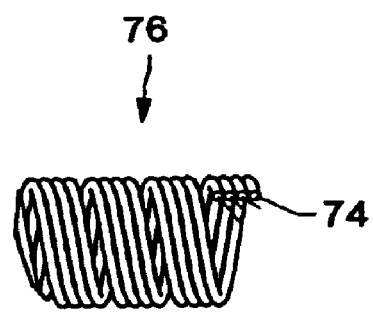
FIG. 4a shows a multi-filar coil single extension conductor embodiment.
Figure 4B:
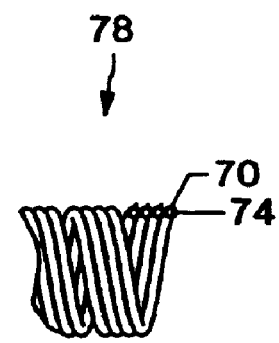
FIG. 4b shows a multi-filar coil multi-extension conductor embodiment.

FIGS. 4a–4b show multi-filar coil extension conductor 60 embodiments. The extension conductor 60 can have a wide variety of configurations in the extension body 54 to meet the needs of the extension 28. At least one extension conductor 60 can be configured as at least one coil 72 in at least one lumen 62 of the extension body 54. In multi-filar coil embodiments where the coil filars 74 are uninsulated (FIG. 4a), the multi-filar coil acts as a single conductor 60. Extension conductors 60 such as shown in FIGS. 3d and 3f can be used to form the multi-filar coil embodiment shown in FIG. 4a. The extension conductor 60 can also have an outer insulator 70. When the coil filars 74 are insulated (FIG. 4b), the each filar 74 can act as an individual conductor 60 and is termed a multi-conductor coil. Extension conductors 60 such as shown in FIGS. 3e and 3g can be used to form the multi-filar coil embodiment shown in FIG. 4b. The coil can have at least one filar 74 and some embodiments can have two, four, eight, sixteen, or more filars 74. There can be at least one extension conductor 60 configured as at least one linear wire in at least one lumen 62. In the linear wire embodiments (FIGS. 5b–5c), each filar 74 is an extension conductor 60. The linear wire can have more than one strand, and the linear wire can have an outer insulator 70. Depending on the extension body 54 embodiment, the conductor 60 may or may not be insulated. In each case, at least one conductor 60 connects at least one extension proximal contact 56 to at least one extension distal contact 58.

Figure 5A:
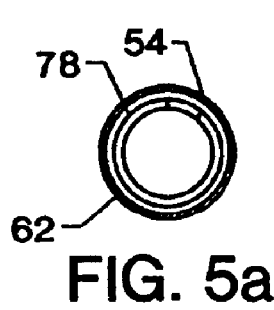
FIG. 5a shows a multi-conductor coil extension conductor embodiment.
Figure 5B:
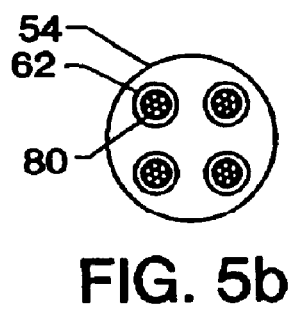
FIG. 5b shows a multi-lumen linear extension conductor embodiment.
Figure 5C:
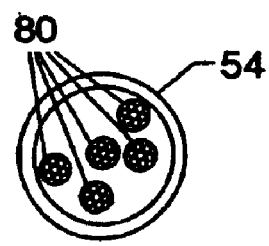
FIG. 5c shows a multi-conductor linear extension conductor embodiment.

FIGS. 5a–5c show various alternate extension body embodiments. The extension body 54 can have at least one lumen 62, and the extension body 54 can be configured with a separate lumen 62 for each filar 74. Some extension bodies 54 embodiments can be configured with between two and sixteen lumens 62. FIG. 5a shows a cross-sectional view of a multi-conductor coil 78 extension body 54 embodiment. The multi-conductor coil 78 is contained in a single lumen 62 tubing extension body 54. Each filar 74 of the coil 78 is insulated providing at least as many conductors 60 as filars 74. FIG. 5b shows a cross-sectional view of a linear wire 80 extension body 54. Each multi-strand 64 filar resides in a lumen 62 of an extension body 54 that has more than one lumen 62. The physical separation provided by the extension body 54 isolates the wire conductors 60 from each other. Additionally, the linear wire 80 may be electrically insulated to provide redundant electrical insulation.

FIG. 5c shows a cross-sectional view of a linear wire 80 in a single lumen 62 extension body 54. Each linear wire 80 is individually insulated to provide electrical isolation between conductors 60 and contained within the extension body 54. In all embodiments (FIGS. 5a–5c), at least one conductor 60 electrically connects at least one extension proximal contact 56 to at least one extension distal contact 58.

Thus, embodiments of the low impedance extension 28 for a neurological stimulator 30 are disclosed to increase energy efficiency and provide many other improvements. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An low impedance conductor for a low impedance extension, comprising:

an outer surface selected for mechanical properties of flexibility and electrical connections having an outer impedance; and, an inner core selected for conductivity having a core impedance that is substantially lower than the outer impedance;

wherein the inner core an outer surface have a composite resistance in the range from about 0.05 to about 0.3 ohms per centimeter.

2. The low impedance conductor as in claim 1, wherein the extension conductor is constructed of drawn filled tubing.

3. The low impedance conductor as in claim 1, wherein the extension conductor is constructed of more than one wire strand.

4. The impedance conductor as in claim 1, wherein the extension conductor has an outer insulator surrounding the outer surface of the extension conductor.

* * * * *

UNITED STATES PATENT AND TRADEMARK OFFICE
CERTIFICATE OF CORRECTION

PATENT NO. : 6,950,709 B2  Page 1 of 1
APPLICATION NO. : 10/686108
DATED : September 27, 2005
INVENTOR(S) : Michael D. Baudino It is certified that error appears in the above-identified patent and that said Letters Patent is hereby corrected as shown below:

Col. 6, Line 1: "an outer" should read --and outer--

Col. 6, Line 11: "The impedance" should read --The low impedance--

Signed and Sealed this

Sixteenth Day of December, 2008

JON W. DUDAS
*Director of the United States Patent and Trademark Office*